United States Patent [19]

Wilkes et al.

[11] Patent Number: 5,634,914
[45] Date of Patent: Jun. 3, 1997

[54] CELLULOSIC FIBRE

[75] Inventors: Andrew G. Wilkes; Alan J. Bartholomew, both of Coventry, United Kingdom

[73] Assignee: Courtaulds PLC, United Kingdom

[21] Appl. No.: 428,683

[22] Filed: Apr. 25, 1995

Related U.S. Application Data

[62] Division of Ser. No. 230,881, Apr. 20, 1994, abandoned, which is a continuation of Ser. No. 965,623, Oct. 22, 1992, abandoned, which is a continuation of Ser. No. 680,597, Mar. 29, 1991, abandoned, which is a continuation of Ser. No. 226,046, Jul. 29, 1988, abandoned.

[30] Foreign Application Priority Data

Jul. 30, 1987 [GB] United Kingdom ............. 8718081

[51] Int. Cl.$^6$ .................... A61F 13/15; A61F 13/20
[52] U.S. Cl. .................... 604/375; 604/367; 604/374; 604/384
[58] Field of Search .................... 604/358, 374–375, 604/365–367, 366, 384–385.1, 370; 428/358–359, 370, 373

[56] References Cited

U.S. PATENT DOCUMENTS

| | | |
|---|---|---|
| 1,773,969 | 8/1930 | Dreyfus et al. . |
| 2,002,153 | 5/1935 | Mendel . |
| 2,880,726 | 4/1959 | Stieg ........................ 604/375 |
| 3,626,045 | 12/1971 | Woodings . |
| 3,670,069 | 6/1972 | Mitchell et al. . |
| 3,889,678 | 6/1975 | Chatterjee et al. . |
| 3,986,511 | 10/1976 | Olofsson et al. . |
| 4,076,933 | 2/1978 | Turbak et al. . |
| 4,081,884 | 4/1978 | Johst et al. . |
| 4,129,679 | 12/1978 | Woodings . |
| 4,165,743 | 8/1979 | Denning . |
| 4,187,342 | 2/1980 | Holst et al. . |
| 4,242,405 | 12/1980 | Bockno . |
| 4,245,000 | 1/1981 | Bockno . |

(List continued on next page.)

FOREIGN PATENT DOCUMENTS

| | | |
|---|---|---|
| 369259 | 5/1990 | European Pat. Off. . |
| 1491169 | 6/1969 | Germany . |
| 2018071 | 2/1971 | Germany . |
| 61-113812 | 5/1986 | Japan . |
| 156049 | 6/1971 | New Zealand . |
| 318631 | 8/1930 | United Kingdom . |
| 1333047 | 10/1973 | United Kingdom . |
| 1387915 | 3/1975 | United Kingdom . |
| 1393778 | 5/1975 | United Kingdom . |
| 2042970 | 10/1980 | United Kingdom . |
| 2085304 | 4/1982 | United Kingdom . |
| 2094637 | 9/1982 | United Kingdom . |
| WO80/00554 | 4/1980 | WIPO . |
| WO89/07924 | 9/1989 | WIPO . |
| WO89/07925 | 9/1989 | WIPO . |
| 9306806 | 4/1993 | WIPO ................ 604/375 |

OTHER PUBLICATIONS

English Translation of Appeal filed Nov. 4, 1994 by Opposer Lenzing in corresponding European Patent No. 301,874 Opposition.

E. Treiber, *Chemiefasern*, 17:344–348 (1967) (with English translation).

Expert Opinion of Dr. Eric Treiber filed in Opposition as of European Patent No. 301,874 and English translation.

Response of patentee, filed Jul. 18, 1995 in Opposition of European Patent No. 301,874.

(List continued on next page.)

*Primary Examiner*—Jonn G. Weiss
*Assistant Examiner*—P. Zuttarelli
*Attorney, Agent, or Firm*—Howson and Howson

[57] ABSTRACT

Viscose filaments, preferably in staple fibre form, which have a decitex of less than 5.0 and a multi-limbed cross-section, the limbs having a length-to-width aspect ratio of at least 2:1. Examples of multi-limbed cross-sectional shapes are Y—, X—, H— and T— shapes. The fibre can be formed into woven, non-woven or knitted fabrics, and is especially useful for absorbent products.

18 Claims, 5 Drawing Sheets

U.S. PATENT DOCUMENTS

| | | |
|---|---|---|
| 4,307,721 | 12/1981 | Tsuchiya et al. ............ 604/375 |
| 4,362,159 | 12/1982 | Sakurai et al. . |
| 4,388,260 | 6/1983 | Bockno . |
| 4,402,899 | 9/1983 | Hartmann et al. . |
| 4,627,849 | 12/1986 | Walton et al. . |
| 4,661,101 | 4/1987 | Sustmann . |
| 5,171,235 | 12/1992 | Theis et al. . |
| 5,358,679 | 10/1994 | Parekh et al. . |
| 5,364,383 | 11/1994 | Hayes et al. . |

OTHER PUBLICATIONS

E. Zihmisch, "Einfluz des Alkaliverhaltnisses auf den Spinnvorgang und auf die Physikalischen Eigenschaften von Viskosefasern", *Faserforschung und Textiltechnik*, 16:443–449 (1965) (filed by patentee in Opposition of European Patent No. 301,874) No translation.

A. Ernst, "Die Vershciedenen Einsatzmoglich–keiten von Modalfasern", *Lenzinger Berichte*, pp. 13–18 (Feb. 1982) (filed by patentee in Opposition of European Patent No. 301,874) No Translation.

E. Treiber, "Strecthing, Drawing and Modified Cross–Section in Viscose Spinning", *Chemiefasern*, 5:344–348 (1967) (English translation) [Treiber I].

E. Treiber, "Stand und Entwicklungen bei Viskosefaserstoffen", *Cellulose Chemistry and Technology*, 2:53–66 (1968) [Treiber II].

E. Treiber et al, "Kring Forskning och Utveckling —Die neue Universal–Laboratoriumsspinnmaschine am schivedischen Holzforsclungsinstitut", *Svensk Papperstidning*, 10:344–347 (May 31, 1970) [Treiber III].

R. Moncrieff, "Man–made Fibres", 5th edition, Heywood Books, p. 179 (1970).

"Textile Terms and Definitions", 8th edition, *The Textile Institute Textile Terms and Definitions Committee*, ed. S. R. Beech et al, pp. 56, 96, 239, and 258 (Sep., 1988).

Albin F. Turbak, "Solvent Spun Rayon, Modified Cellulose Fibers and Derivatives", *ACS Symposium Series 58*, Meeting of the American Chemical Society, New Orleans, LA, Mar. 21–23, Chapters 4 and 6 only (1977).

J. Gordon Cook, "Man–made Fibres", *Handbook of Textile Fibres*, Merrow Publishing Co. Ltd., Fourth Edition, pp. 58–59 and 77–78 only (1968).

The Textile Institute, "Textile Terms and Definitions", Eighth Edition, ed. Beech et al, pp. 200, 273 and 297 only (Sep., 1988).

R. W. Moncrieff, "Man–Made Fibres", *Heywood Books*, Fifth Edition, pp. 272–273 only (1970).

Kirk–Othmer, Encyclopedia of Chemical Technology, 3rd ed., vol. 19, p. 855 (Sep., 1982).

J. Ratcliffe et al, "Courtaulds Develops Specialised Nonwovens Fibres", *Nonwovens Yearbook*, pp. 1, 28, 30 (Aug., 1984).

Wagner, "Die Textilen Rohstoffe", Deutscher Fachverlag, Frankfurt, 6th edition, pp. 156–157 (and partial English translation of these pages) (Feb., 1981).

Opposition Papers filed by Dr. Albin Schwarz on behalf of Lensing Aktiengesellschaft (Mar. 12, 1993).

Oppostion Papers filed by W. Wehnert on behalf of Hoechst AG (Mar. 12, 1993).

K. Gotze, *Chemiefasern, nach dem Viskoseverfahren*, Springer–Verlag, Publ., Berlin, p. 641 (1967).

Kirk–Othmer's "Encyclopedia of Chemical Technology", vol. 19, 3rd ed., John Wiley & Sons, New York, pp. 863 and 872 (1982).

CELLULOSIC FIBRE

This is a divisional of U.S. patent application No. 08/230,881 filed on Apr. 20, 1994, now abandoned which is a continuation of U.S. patent application No. 07/965,623 filed on Oct. 22, 1992 and now abandoned, which is a continuation of U.S. Pat. application No. 07/680,598 filed on Mar. 29, 1991 and now abandoned, which is a continuation of U.S. patent application No. 07/226,046 filed on Jul. 29, 1988 and now abandoned.

This invention relates to regenerated cellulosic filaments, particularly viscose filaments, which have a multi-limbed cross-section, to fiber comprising such filaments and to products formed therefrom.

One advantage of multi-limbed viscose filaments over conventional circular cross-sectional viscose filaments is their greater bulk, because the circumferential area of the multi-limbed filaments is larger than their actual cross-sectional area. For example, Japanese Patent Application Kokai 61-13812 describes a filament yarn consisting of X- or Y-shaped continuous viscose filaments that is used in textile applications where bulk is important, for example in pile weaves.

Another advantage of multi-limbed viscose filaments is their increased absorbency over conventional filaments. Thus, multi-limbed filaments in staple fiber form are particularly useful for absorbent products, for example tampons, towels and swabs. Absorbent viscose fiber is described in UK Patent 1 333 047 in which the filaments have a collapsed hollow structure and a multi-limbed cross-section. Although these filaments have a relatively high absorbency compared- with conventional viscose filaments, they have the disadvantage that they are complicated to manufacture, as the filaments must be formed with an inflated, hollow structure and subsequently collapsed. The process also has the disadvantage that the collapse of the fiber is difficult to control sufficiently to ensure a uniform filament cross-section, and therefore the resulting filaments have irregular multi-limbed cross-sectional shapes. The filaments also have a relatively low tenacity.

The present invention provides a solid filament of regenerated cellulosic material having a decitex of less than 5.0 and a multi-limbed cross-section, each limb having a length-to-width aspect ratio of at least 2:1.

The length-to-width aspect ratio of the filament limbs is generally from 2:1 to 10:1, preferably from 2:1 to 7:1, and more preferably from 3:1 to 5:1. In general, the higher the aspect ratio, the higher the degree of free volume of the filaments. This gives a high degree of absorbency when the filaments are in staple fiber form, provided that the limbs are not so long and thin that they bend back upon themselves.

The filament according to the invention preferably has 3 or 4 limbs, although it may have more than 4 limbs if desired, and also preferably has a cross-sectional shape that is generally (i.e. largely) symmetrical about at least one axis, as in a Y—, X—, H— or T— shaped filament cross-section, although other shapes are also included within the scope of the invention. Preferably, the filament has a Y-shaped cross-section. The angle between the limbs varies according to the cross-sectional shape and can be, for example, from 5° to 180°, although, it is preferred that the filament cross-section is as regular as possible.

As mentioned above, the filament according to the invention has a low decitex of less than 5.0, a low decitex being advantageous for high absorbency products. Generally the decitex is between 0.5 and 5.0, but more preferably is between 1.5 and 4.0.

Filaments according to the invention are advantageously produced in the form of staple fiber, and the invention further provides such staple fiber. The combination of the multi-limbed cross-sectional shape and the low decitex gives filaments which in staple fiber form exhibit a high absorbency. Surprisingly, we have found that, although the filaments have a solid structure as opposed to a collapsed hollow structure characteristic of the fiber of UK Patent 1,333,047 mentioned above, the fiber of the invention has an absorbency which can match and in some product forms exceed the absorbency of the fiber of the said UK patent, even though its water imbibition is considerably lower. Usually the fiber according to the invention has a total free absorbency (TFA) of at least 24 grams of water per gram of the fiber using the test as set out in British Pharmacopoeia 1980, Standard Methods (BP 1980, SDM.) XI.A, p.928. For instance, a TFA in the range up to 28 g/g can be obtained. In addition the fiber of the invention has high bulk, a cotton-like handle, and a tenacity approximately equivalent to conventional circular cross-sectional viscose filaments for a given viscose composition and decitex.

The staple fiber according to the invention preferably comprises multi-limbed filaments substantially all of which have substantially the same cross-sectional shape. This enables the fiber properties, such as absorbency and bulk, to be more readily controlled. However, if desired, the staple fiber may comprise a mixture of filaments of two or more different cross-sectional shapes provided that at least some of the filaments have a multi-limbed cross-section characteristic of the filaments of the invention.

Preferably, the filaments according to the invention are viscose, and they are conveniently spun from a standard viscose composition using standard viscose spinning conditions, with the exception that multi-limbed shaped extrusion holes in the spinnerette are substituted for the conventional circular shaped holes. As the filaments produced have a solid rather than a hollow structure, the disadvantages involved in producing hollow filaments are avoided.

The viscose composition used for spinning the filaments of the invention may be a commonly used viscose, typically having a cellulose content of 5 to 12% by weight and a caustic soda content of 4 to 10%, preferably 5 to 7%, by weight. Filaments may be spun over the full range of salt figures, although viscose having a salt figure of 4.0 to 12.0 is generally used. The ball-fall viscosity of the viscose can be from 15 to 180 seconds at 18° C., but is preferred to be from 45 to 55 seconds.

The filaments are spun through extrusion holes having a multi-limbed shape similar to the desired shape of the filaments. Typically the spinnerette is made from a gold-platinum alloy and the extrusion holes formed by conventional methods such as spark erosion or mechanical punching. To achieve filament limb aspect ratios of at least 2:1 together with a filament decitex of less than 5.0 the dimensions of the limbs of the extrusion holes are preferably between 50 µm and 250 µm long and between 20 and 40 µm wide.

The filaments are spun into a spin bath which can conveniently be of a standard spin bath composition for viscose spinning. Typically this composition includes by weight zero to 3%, preferably 0.5 to 2%, zinc sulphate, 6 to 20%, preferably 7 to 10%, sulfuric acid and 10 to 28%, preferably 20 to 26%, sodium sulphate. The spin bath temperature is generally between 50° and 60° C., although higher and lower temperatures may be used.

We have found that, for absorbent products such as tampons, even higher absorbencies can be achieved by adapting the process to give a slower rate of filament regeneration. The regeneration rate can be slowed down by altering one or more or the spinning conditions, for example by decreasing the acid level and/or increasing the sulphate level. Alternatively, or in addition, the viscose can be modified by a viscose modifier which is usually added to the viscose prior to spinning. Any of the commonly available viscose modifiers may be employed, examples being polyalcohols, soluble dithiocarbonates, soluble aliphatic and alicyclic amines, oxyethanols and quinoline. Polyglycols are preferred, especially PEG-1500 (polyethylene glycol where 1500 indicates the average molecular weight of the chain).

After spinning, the filaments are stretched, and then preferably cut into staple lengths, washed and dried using conventional techniques to give staple fiber.

The low decitex, multi-limbed filaments in staple fiber form can be used in a wide range of textile and other applications which take advantage of the fiber's high absorbency, bulk, cover and/or cotton-like handle. These applications include, for example, tampons, swabs and waddings, woven fabrics, knitted fabrics and non-woven fabrics. Non-woven fabrics can be produced by, for example, latex bonding, powder bonding, thermal bonding or hydroentanglement. The fiber is especially useful for tampons and similar products because the fiber has the combined advantages of high absorbency and satisfactory compressional stability. In general, tampons are manufactured in one of two forms; longitudinally expanding or radially expanding. For either type the absorbency of the tampon is linked to its stability, in that any modification made to the tampon fiber to increase its absorbency generally has the effect of decreasing its stability. A tampon formed from fiber according to the invention has the advantage that it can be manufactured to have an acceptable stability together with high absorbency.

Thus a longitudinally expanding tampon formed from fiber according to the invention can be manufactured to have a stability of approximately 15 mm as measured by the 'expansion test' as hereinafter defined, and an absorbency of at least 4.3 grams 1% saline solution per gram of fiber, and often at least 4.5 g/g and up to about 5.5 g/g, as measured by a 'modified Syngina' test as hereinafter defined.

Likewise, a radially expanding tampon formed from fiber according to the invention can be manufactured to have a stability of at least 3.2 decaNewtons (daN), often 3.8 daN or more, e.g. up to about 8.0 daN, as measured by the 'crush test' as hereinafter defined, and an absorbency of at least 4.5 g/g, often at least 5.0 g/g and up to about 6.0 g/g,. as measured by a 'modified Syngina' test as hereinafter defined.

In addition tampons having a higher stability can be formed from fiber according to the invention. Thus, longitudinally expanding tampons can be manufactured that have a stability of 10 mm or less, and radially expanding tampons can be manufactured having a stability of 5.0 daN or more.

Products formed from the fiber may contain solely fiber according to the invention or may be blended with other fibers. These other fibers may be cellulosic fibers, such as standard viscose or cotton, or non-cellulosic such as polyester. In addition, the fiber of the invention may be incorporated in a product in only one cross-sectional shape, for example solely Y-shaped, or, alternatively, two or more different cross-sectional shapes can be used.

The invention is illustrated by the following Examples and with reference to the accompanying drawings in which.

All percentages given are by weight unless otherwise specified.

EXAMPLE 1

Figure 1:
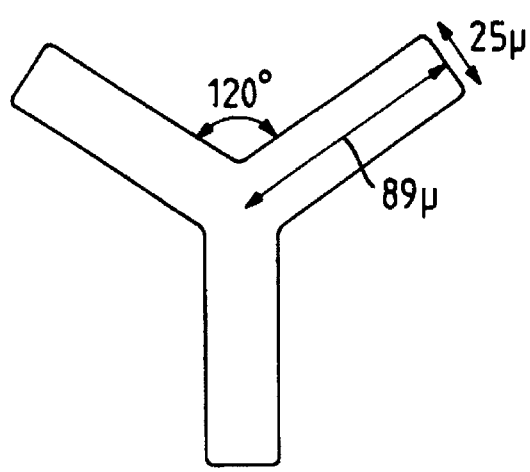
FIGS. 1, 6 and 8 are diagrammatic representations of extrusion holes used for spinning filaments according to the invention.

A 14,364 filament viscose tow comprising 9.0% cellulose and 6.0% caustic soda, with a salt figure of 5.6 and a ball-fall viscosity of 45 seconds at 18° C., was spun through Y-shaped extrusion holes, the dimensions of the limbs of the holes being 89 μm long and 25 μm wide with equivalent limb-to-limb angles of 120° as shown diagrammatically in FIG. 1. The filaments were spun into a spin bath comprising 7.5% sulfuric acid, 0.8% zinc sulphate, 24.5% sodium sulphate and 67.2% water to form a tow of filaments having an average filament decitex of 2.2. The spinning speed was 50 m per minute and the viscose extrusion rate was 1068 millilitres per minute (ml/min). The tow was stretched by 45% in a 2% aqueous sulfuric acid solution at 95° C., cut to staple lengths of 38 mm and washed and dried.

Figure 4:
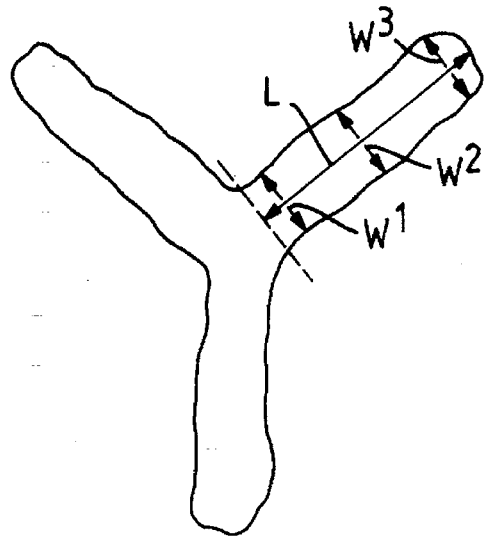
FIG. 4 shows the measurements taken to determine the aspect ratio of a filament limb.
Figure 2:
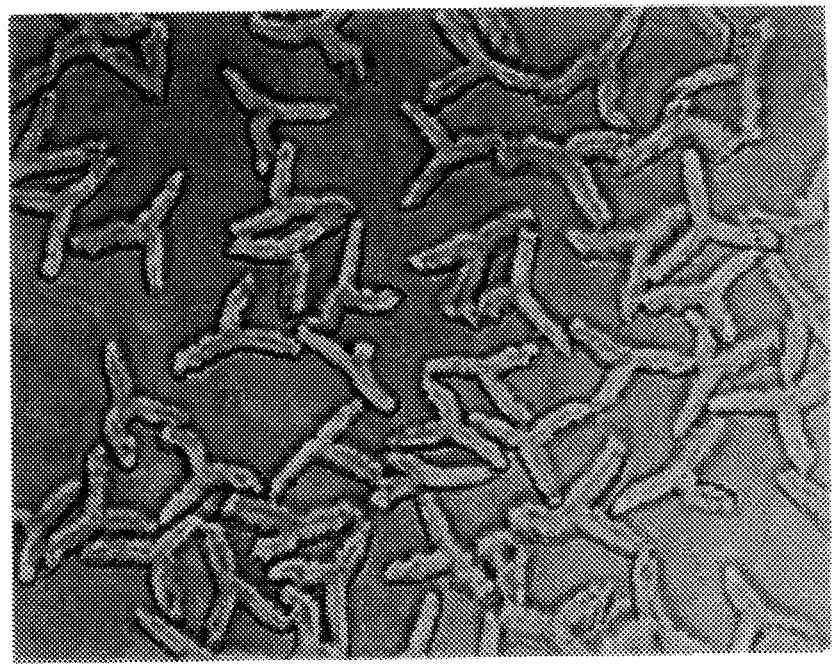
FIGS. 2, 3, 5, 7 and 9 are reproductions of photographs of filament cross-sections.
Figure 3:
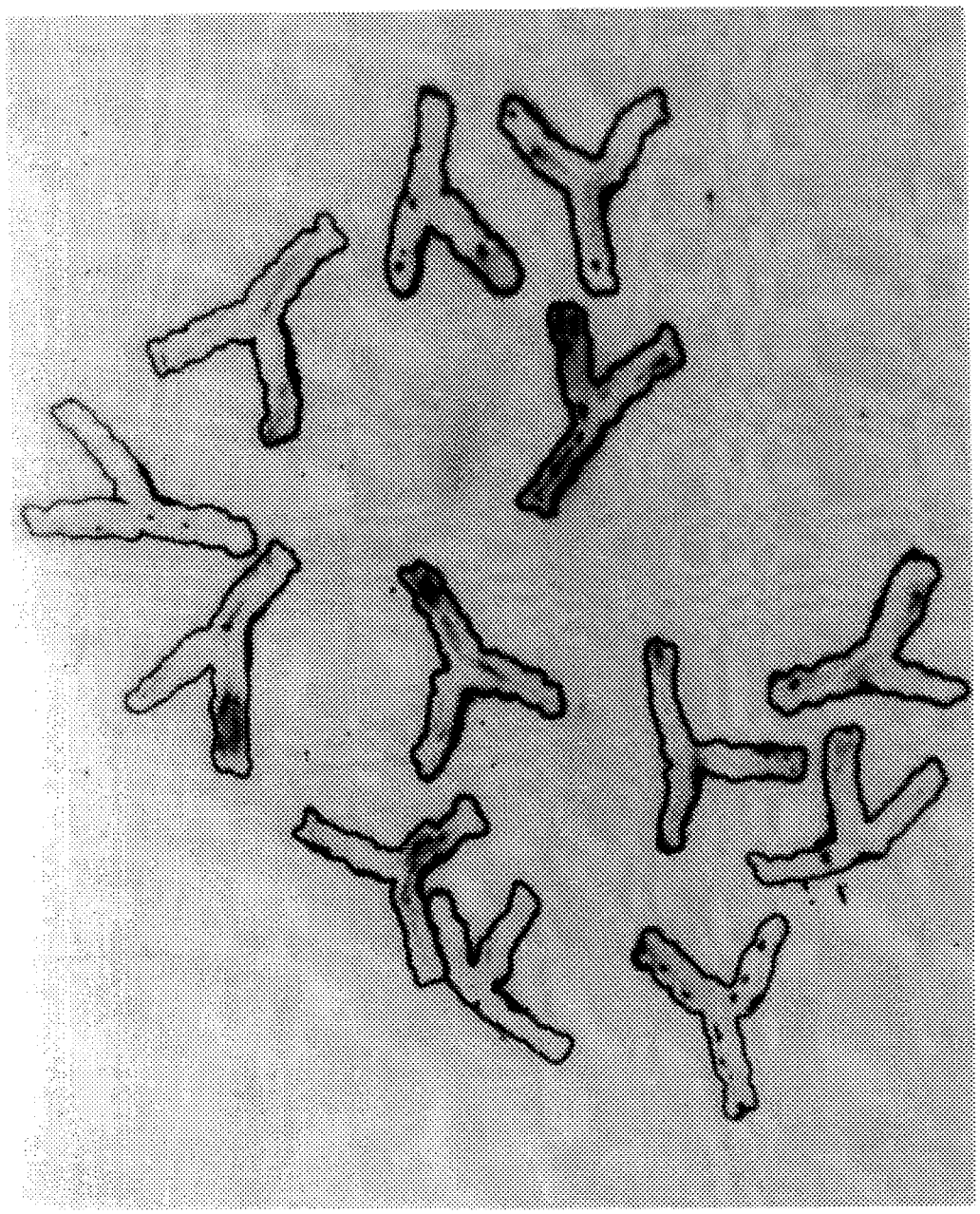

The cross-sectional shapes of the resulting filaments is shown magnified 500 times in FIG. 2 and magnified 1240 times in FIG. 3. The solid filaments have a well-defined Y-shape with a much higher degree of regularity than the filaments described in UK Patent 1 333 047 mentioned above. The length-to-width aspect ratio of the resulting filaments was between 3:1 and 4:1. This aspect ratio is determined by measuring the length 1 and width w of the limbs as exemplified in FIG. 4. For each limb measured, one length measurement and three width measurements are taken. The widths are measured at approximately the middle and at either end of the limb and then the average width of the limb is calculated from these three measurements. The aspect ratio is given as the ratio of the length l to average width w. Using the standard test defined in BP 1980, SDM.XI.A, p.128, the staple fiber was found to have a total free absorbency (TFA) of 25.6 gram of water per gram of fiber. The fiber also possessed an average water imbibition of 120%, a filament tenacity of 18 cN/tex and an extensibility of 23.5%.

To determine the water imbibition value of the filaments, a 1 g sample of dried filaments is soaked in water at a temperature of 20° C. for 15 minutes, centrifuged at a force of 10,000 Newton for 5 minutes, weighed, dried at a temperature of 110° C. for 2.5 hours and finally re-weighed. Water imbibition is then defined as follows:

weight of wet filaments—weight of dry filaments×100%
weight of dry filaments

EXAMPLE 2

Y-shaped viscose fiber was produced as described in Example 1 with the following modifications:

Viscose salt figure: 6.0

Viscose modifier: 3% PEG-1500 added to viscose prior to spinning (no modifier added in Example 1)

Zinc sulphate in spin bath: 1.5%

Tow Stretch 50% in air

Viscose extrusion
  rate : 1359 ml/min

Figure 5:
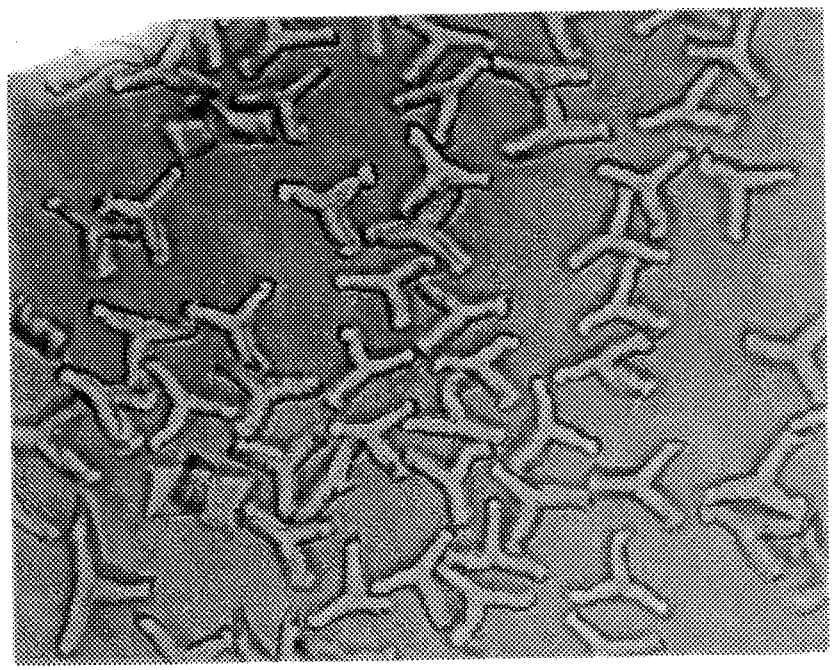

The resulting filaments were solid and had a well-defined, uniform Y-shaped cross-section as can be seen from the photograph of the filaments, magnified 500 times, in FIG. 5. The filaments had a decitex of 2.8 and a limb aspect ratio of 3:1 to 4:1. Using the same test as in Example 1, the staple fiber have a TFA of 25.4 g/g and a water imbibition of 113%. The filament tenacity was 16.7 cN/Tex and the extensibility 21.5%.

EXAMPLE 3

A 16,568 filament viscose tow having the same composition as that described in Example 1 was spun through Y-shaped extrusion holes, the dimension of the limbs being 70 μm long and 25 μm wide with equivalent limb-to-limb angles of 120°. The filaments were spun into a bath comprising 9.0% sulfuric acid, 0.8% zinc sulphate, 24.0% sodium sulphate and 66.2% water at 50° C. to form a tow of filaments having an average decitex of 1.3. The spinning speed was 50 m/min and the viscose extrusion rate was 726 ml/min. The tow was stretched by 50% in a 2% aqueous sulfuric acid solution at 95° C., cut to a staple length of 38 mm and washed.

The resulting filaments were solid and had a well defined Y cross-section with a limb aspect ratio between 3:1 and 4:1. The staple fiber had a TFA of 25.8 g/g, a water imbibition of 125%, a filament tenacity of 18.3 cN/tex and an extensibility of 25.2%.

EXAMPLE 4

A 14,364 filament viscose tow was produced as described in Example 3 except that the viscose was spun from Y-shaped extrusion holes with limbs 89 μm long and 25 μm wide and the viscose extrusion rate was 2184 ml/min to form a tow of filaments having an average decitex of 4.5.

The resulting solid filaments had a well defined Y cross-section with a limb aspect ratio above 2:1, a TFA of 26.0 g/g, a water imbibition of 104%, a filament tenacity of 19.0 cN/tex and an extensibility of 22.8%.

EXAMPLE 5

Staple fibers produced as described in Examples 1 and 2 were each formed into two types of tampon: a longitudinally expanding tampon having an average weight of about 2.72 g and an average density of about 0.35 g/cm³; and a radially expanding tampon having an average weight of about 2.8 g and an average density of 0.46 g/cm³.

The surface properties of the fiber were modified by the addition of a glycerol finish in order to obtain a tampon having a stability of approximately 15 mm for the longitudinally expanding tampons, and approximately 3.5 to 7.0 decaNewtons (daN) for the radially expanding tampons.

The stability of a longitudinally expanding tampon is measured by the 'expansion test' whereby the tampon is maintained in a controlled environment after manufacture and the increase in the length of the tampon in millimetres is measured.

The stability of a radially expanding tampon is measured using the 'crush test' which measures, decaNewtons (daN), the longitudinal force required to buckle the tampon. The cylindrical tampon is placed with one end on a fixed lower jaw of a test machine, the upper moveable jaw is brought down to contact the other end of the tampon and is then set to move down at a speed of 5 cm/min. The force exerted by the tampon on the jaws of the test machine is measured continuously and the point at which this force begins to fall instead of rise is the point at which the tampon buckles. The maximum force achieved is the stability of the tampon. During the test the tampon is maintained in a controlled environment of 65% RE and 20° C.

The absorbency of each tampon was then tested using a 'modified Syngina' test. For the radially expanding tampons the test used was as defined in UK Patent 2 094 637B, pp. 4–6 except that a 200 mm hydrostatic head air pressure was employed. For the longitudinally expanding tampons the test was used as defined in the said patent with the further modification that 1 180 mm hydrostatic head water pressure was employed, the Syngina chamber was tilted at 30° to the vertical and the saline solution was injected into the top of the tampon, using a hypodermic needle, at a rate of 50 mm/hour. For both tampon types the absorbency was tested with a 1% saline solution.

The absorbencies were compared with those of tampons formed from standard, circular cross-section viscose fiber spun from equivalent viscose compositions and spinning conditions and finished in order to obtain stability approximately 15 mm and 3.5 to 7.0 daN for longitudinally and radially expanding tampons respectively. The absorbencies were also compared with those of tampons formed from collapsed hollow viscose fiber produced according to UK Patent 1 333 047. The water imbibition of each fiber type was also measured.

The results are given in Tables A and B, where 'Y-shaped (1)' and 'Y-shaped (2)' denote tampons formed from the staple fiber of Examples 1 and 2 respectively, 'Standard (1)' and 'Standard (2)' denote tampons spun from standard staple viscose fiber produced from viscose compositions and using spinning conditions equivalent to those of Examples 1 and 2 respectively, and 'Collapsed Hollow' denotes a tampon produced from staple fiber according to UK Patent 1 333 047.

TABLE A

| | Longitudinally Expanding Tampon | | |
|---|---|---|---|
| Fiber Type | Absorbency (g/g) | Stability (mm) | Water Imbibition (%) |
| Y-shaped (1) | 4.35 | 15 | 120 |
| Standard (1) | 3.82 | 14 | 103 |
| Y-shaped (2) | 4.76 | 15 | 113 |
| Standard (2) | 3.96 | 15 | 88 |
| Collapsed Hollow | 4.47 | 12 | 270 |

The results in Table A show that longitudinally expanding tampons formed from the fiber according to the invention have, for a given stability, a much higher absorbency than tampons formed from equivalent standard viscose fiber. Furthermore, when the fiber of the invention is spun using a modified viscose composition as in Example 2, then the resulting tampon also has an absorbency higher than that achieved using collapsed hollow viscose fiber, even though the water imbibition of the collapsed hollow fiber is more than double that of the fiber of the invention.

TABLE B

| | Radially Expanding Tampon | | |
|---|---|---|---|
| Fiber Type | Absorbency (g/g) | Stability (daN) | Water Imbibition (%) |
| Y-shaped (1) | 4.76 | 3.8 | 120 |
| Standard (1) | 3.98 | 3.5 | 103 |
| Y-shaped (2) | 5.53 | 7.0 | 113 |
| Standard (2) | 3.82 | 4.0 | 88 |
| Collapsed Hollow | 5.30 | 3.2 | 270 |

The results in Table B show that radially expanding tampons formed from fiber according to the invention have a markedly greater absorbency than tampons formed from standard fiber. This is particularly noticeable when 'Y-shaped (2)' fiber is used as this tampon has superior absorbency as well as superior stability over tampons formed from both standard and collapsed hollow viscose fiber.

EXAMPLE 6

The staple fibers of Examples 1 and 2 were each formed into tampons as described in Example 5 except that no finish was added to the fiber to rigidify its surface properties, and hence no alteration was made to the 'natural' stability of the tampons.

These stabilities were compared with those of tampons from unfinished equivalent standard viscose fibers. The results are given in Table C.

TABLE C

| Fiber Type | Tampon Type | Stability |
| --- | --- | --- |
| Y-shaped (1) | Radially Expanding | 5.4 daN |
| Standard (1) | Radially Expanding | 3.6 daN |
| Y-shaped (1) | Longitudinally Expanding | 9 mm |
| Standard (1) | Longitudinally Expanding | 16 mm |
| Y-shaped (2) | Radially Expanding | 7.0 daN |
| Standard (2) | Radially Expanding | 4.0 daN |
| Y-shaped (2) | Longitudinally Expanding | 7 mm |
| Standard (2) | Longitudinally Expanding | 15 mm |

These results show that for both tampon types, the fiber according to the invention has considerably greater stability than standard fiber. This is especially evident in tampons formed from fiber type 'Y-shaped (2)'.

EXAMPLE 7

A viscose having the same composition as that described in Example 1 was spun through Y-shaped extrusion holes, as specified in Example 1, into a spin bath comprising 10.5% sulfuric acid, 0.7% zinc sulphate, 24.0% sodium sulphate and 64.8% water to form a tow of Y-shaped filaments having an average filament decitex of 2.4 and a limb aspect ratio between 3:1 and 4:1. The tow was stretched by 50% in a 2% aqueous sulfuric acid solution at 95° C., cut to staple lengths of 38 mm, washed and dried.

The resulting fiber was blended with a 1.7 decitex polyester, 'SD Grilene B', to form a 50% viscose, 50% polyester by weight yarn having a 1/30 s cotton count. The fiber was made up into a knitted fabric with a dropped needle interlock construction. The fabric weighed 340 g/m and had a thickness of 2.0 mm.

The rate of absorbency, bulk, drapability, and flexural rigidity of the fabric were measured using the following tests:

Rate of absorbency: This was measured using the 'Plate Test' as defined in a paper entitled 'A Survey and Comparison of Laboratory Test Methods for Measuring Wicking' by P. R. Harnett and P. N. Mehta, Textile Research Journal, July 1984, pp 471–478. The fabric was washed and immersed in water and the amount of water absorbed was measured at intervals over 2 minutes.

Bulk: The rate of air flow through a 5 g compressed sample of the fabric was measured on a manometer using the Shirley Micronaire test method, the lower the rate the greater the fabric bulk.

Drapability: The drapability of a fabric is the extent to which it will deform when it is allowed to hang under its own weight. Drapability was measured by determining the drape coefficient of the face and back of the fabric, drape coefficient being the ratio of the projected area of the draped specimen to its undraped area, according to BSI test BS 5058 1973.

Flexural Rigidity: The degree to which the fabric bends under its own weight was measured according to BSI test BS 3356 1961. The flexural rigidity along the length and across the width of the fabric was determined.

The fabric properties were compared with an equivalent standard viscose/polyester knitted fabric wherein the viscose fiber was spun from an equivalent composition and using the equivalent spinning conditions as above except that the filaments were spun through standard, circular cross-section holes. The results are given in Tables D, E and F, where 'Y-shaped' denotes the fabric containing Y-shaped viscose fiber and 'Standard' denotes the fabric containing the standard, circular cross-section viscose fiber.

TABLE D

| Fabric Absorbency | | |
| --- | --- | --- |
| | Absorbency (cm³/g) | |
| Time (secs) | Y-shaped | Standard |
| 15 | 1.53 | 0.22 |
| 30 | 1.88 | 0.62 |
| 60 | 2.10 | 1.35 |
| 90 | 2.17 | 1.63 |
| 120 | 2.19 | 1.77 |

These results show that fabric containing fiber according to the invention has a substantially improved rate of absorbency over equivalent fabric containing standard viscose fiber.

TABLE E

| Fabric Bulk | |
| --- | --- |
| Fabric Type | Air Flow (cm³/sec) |
| Y-shaped | 16.6 |
| Standard | 24.4 |

The air flow through the fabric containing the Y-shaped fiber is considerably lower than the air flow through the standard fabric which shows the higher bulk of the fabric containing fiber according to the invention.

TABLE F

| Drapability and Flexural Rigidity | | |
| --- | --- | --- |
| | Y-Shaped | Standard |
| Drape coefficient: | | |
| face | 0.118 | 0.087 |
| back | 0.126 | 0.106 |
| Flexural rigidity: | | |
| length | 40.0 | 27.3 |
| width | 17.2 | 9.3 |

The higher drape coefficient and higher flexural rigidity of the fabric containing the Y-shaped fiber indicates that this fabric has a stiffer, more cotton-like handle than standard viscose fabrics.

EXAMPLE 8

From fiber produced under the conditions specified in Example 1, latex bonded nonwovens were prepared using a Kidd & Zigrino saturation bonder. A VA/E vinyl acetate-ethylene copolymer (type R32440) (available from Vinamul Limited) was used as the binder at 20% add-on to 100% viscose webs. The bonded fabrics were produced at 40 gsm and evaluated using the following tests:

Bulk: the average thickness of the 40 gsm fabric in mm using the EDANA recommended test for nonwoven thickness 30.2–78.

Overall Dry Strength: the maximum load sustainable by the fabric using the EDANA recommended test for nonwoven tensile strength 20.0–73, where the overall dry strength is taken to be the square root of the product of the individual machine and cross-directional strengths.

Absorbent Capacity: the quantity of water retained by a 4 cm diameter circle of the fabric after total immersion for one minute and draining for 30 secs, in g/g.

Wicking Distance: the capillary water rise (speed of liquid transport) in mm using the EDANA recommended test for nonwoven absorption 10.0–72.

The fabric properties were compared with an equivalent latex bonded fabric produced from standard circular cross-section viscose spun under identical conditions as given for the standard fiber in Example 7.

The results are given in Table G below, where 'Y-shaped' denotes the fabric containing Y-shaped fiber and 'Standard' denotes the fabric containing the standard, circular cross-section viscose.

TABLE G

| Property | Y-shaped | Standard |
|---|---|---|
| Bulk (mm) | 0.23 | 0.17 |
| Overall Dry Strength (daN) | 2.2 | 2.4 |
| Absorbent Capacity (g/g) | 10.6 | 7.3 |
| Wicking Distance (mm) at | | |
| 30 secs | 8 | 3 |
| 60 secs | 11 | 6 |
| 180 secs | 19 | 13 |

EXAMPLE 9

From fiber produced under the conditions specified in Example 1, water jet entangled nonwovens were prepared using a Honeycomb hydroentanglement rig from 100% Viscose webs. The water pressure used to attain full entanglement was of the order of 1500 psi 10,000 kPa).

The bonded fabric was produced at 40 gsm and evaluated using the test methods described in Example 8.

The fabric properties were compared with an equivalent hydroentangled fabric produced from standard circular cross-section viscose spun under identical conditions as given for the standard fiber in Example 7.

The results are given in Table H below, where 'Y-shaped' denotes the fabric containing Y-shaped fiber and 'Standard' denotes the fabric containing the standard, circular cross-section viscose.

TABLE H

| Property | Y-shaped | Standard |
|---|---|---|
| Bulk (mm) | 0.22 | 0.18 |
| Overall Dry Strength (daN) | 1.3 | 1.3 |
| Absorbent Capacity (g/g) | 17.5 | 11.9 |

TABLE H-continued

| Property | Y-shaped | Standard |
|---|---|---|
| Wicking Distance (mm) at | | |
| 30 secs | 5 | 3 |
| 60 secs | 7 | 5 |
| 180 secs | 12 | 8 |

The results given in Tables G and H indicate that for both latex and hydroentangled nonwovens the Y-shaped fiber produces bulkier, more absorbent products which are more able to transport fluid. In hydroentangled nonwovens Y cross-section fiber has the advantage of producing a fabric with a stiffer, more cotton-like handle.

EXAMPLE 10

From fiber produced under the conditions specified in Example 7, 100%.viscose woven fabrics were prepared. The staple fiber was spun into a yarn having a 1/30's cotton count. The yarn was made up into a woven fabric with a 2×2 twill construction. The fabric weighed 320 gsm and had a thickness of 1.8 mm.

The fabric properties were compared with an equivalent standard viscose woven fabric wherein the viscose fiber was spun from an equivalent composition viscose as the Y-shaped fiber using identical spinning conditions.

The results are quoted below for both fabrics; following an evaluation using the test methods outlined previously in Example 7, where 'Y-shaped' again denotes the fabric containing the Y-shaped viscose fiber and 'Standard' denotes the fabric containing the standard, circular cross-section viscose fiber.

TABLE J

| Property | Y-shaped | Standard |
|---|---|---|
| Absorbency (cm³/g) at | | |
| 5 secs | 0.96 | 0.57 |
| 15 secs | 1.38 | 1.15 |
| 30 secs | 1.64 | 1.44 |
| 60 secs | 1.75 | 1.67 |
| 120 secs | 1.78 | 1.71 |
| Air Flow (cm²/sec) | 14.7 | 18.6 |
| Flexural Rigidity (mg · cm) | | |
| length | 53.0 | 45.4 |
| width | 27.1 | 23.7 |

The results show that fabric woven from the Y-shaped viscose fiber has improved properties over fabric woven from standard, circular cross-section viscose fiber.

EXAMPLE 11

Figure 6:
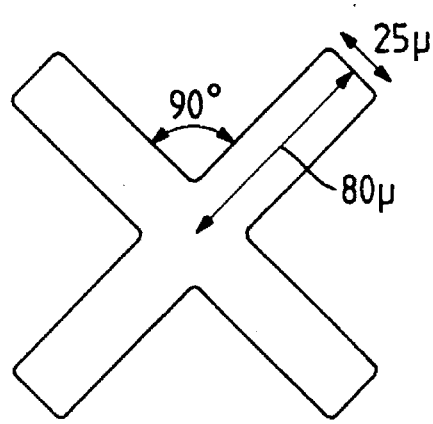

A 5000 filament viscose tow having the same composition as that described in Example 1 was spun through. X-shaped extrusion holes, the dimensions of the limbs being 80 µm long and 25 µm wide, with equivalent limb to limb angles of 90° as shown in FIG. 6. The filaments were spun into a bath comprising 9.5% sulfuric acid, 1.0% zinc sulphate, 24.5% sodium sulphate and 65.0% water at 50° C. to form a tow of filaments having an average decitex of 3.5. The spinning speed was 50 m/min and the viscose extrusion rate was 590 ml/min. The tow was stretched by 50% in a 2% aqueous sulfuric acid solution at 95° C., cut to a staple length of 38 mm and washed.

The resulting solid filaments had a well defined X cross-section, with a limb aspect ratio of between 2:1 and 4:1. The staple fiber had a TFA of 25.0 g/g, a water imbibition of 114%, a filament tenacity of 19.0 cN/tex and an extensibility at break of 25.0%.

EXAMPLE 12

X-shaped fiber was produced as described in Example 11 with the following modifications:

viscose salt figure: 6.0 viscose modifier: 3% PEG-1500 added to the viscose prior to spinning.

zinc sulphate in the spin bath: 1.5%.

Figure 7:
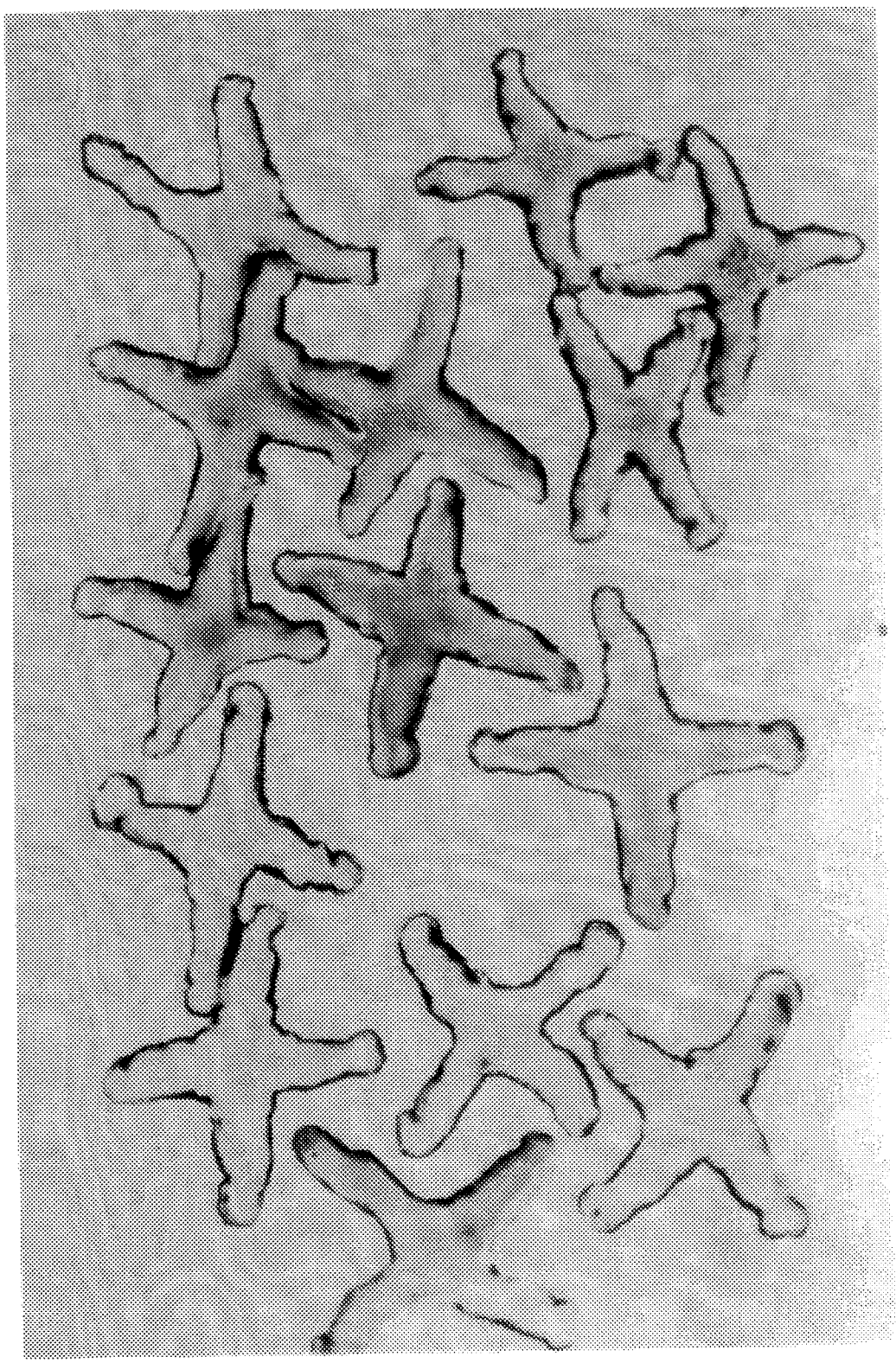

The resulting filaments were solid and had a well defined, uniform X-shaped cross-section as can be seen from the photograph of the filaments, magnified 1624 times, in FIG. 7. The filaments had a decitex of 3.5 and a limb aspect ratio of 3:1 to 4:1. The staple fiber had a TFA of 25.0 g/g and a water imbibition of 107%. The filament tenacity was 16.7 cN/tex and the extensibility was 25.0%.

EXAMPLE 13

Staple X-shaped fibers prepared according to the conditions specified in Examples 11 and 12 were evaluated in longitudinally expanding tampons against standard circular cross-section viscose fibers produced under identical conditions, using the method outlined in Example 5. The surfaces of the fibers were modified by the addition of glycerol finish in order to obtain a tampon having a stability of approximately 15 mm.

The tampon absorbency values were also compared with those for tampons formed from collapsed hollow fibers produced according to UK Patent 1 333 047. The water imbibition of each fiber is specified.

The results are given in Table K below, where 'X-shaped' and 'X-shaped (M)' refer to tampons formed from the staple fiber of Examples 11 and 12 respectively. 'Standard' and 'Standard (M)' denote tampons produced from standard staple viscose fiber spun from viscose compositions and using spinning conditions equivalent to those of Examples 11 and 12 respectively. 'Collapsed Hollow' denotes a tampon produced from staple fiber according to the previously cited patent.

TABLE K

| Fiber Type | Absorbency (g/g) | Stability (mm) | Water Imbibition (%) |
|---|---|---|---|
| X-shaped | 4.26 | 14 | 114 |
| Standard | 3.80 | 15 | 100 |
| X-shaped (M) | 4.64 | 14 | 107 |
| Standard (M) | 3.85 | 15 | 94 |
| Collapsed Hollow | 4.47 | 12 | 270 |

Similar trends are observed to those described in Example 5.

EXAMPLE 14

Figure 8:
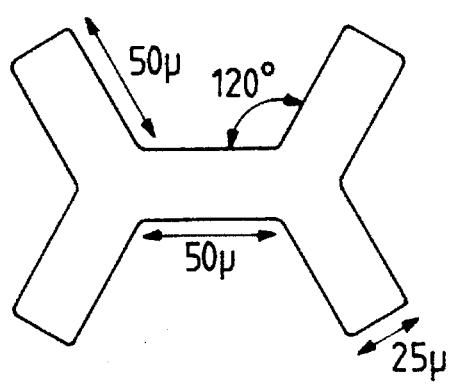

A 5000 filament viscose tow having the same composition as that described in Example 12 was spun through extrusion holes having a shape and dimensions as shown in FIG. 8.

The filaments were spun into a bath comprising 7.5% acid, 1.2% zinc and 23.5% sulphate at 50° C. to form a tow of filaments having an average decitex of 3.3. The spinning speed was 50 m/min and the viscose extrusion rate was 558 ml/min. The tow was stretched by 50% in air, cut to a staple length of 38 mm and washed.

Figure 9:

The resulting solid filaments had a well defined H-shaped cross-section as shown in FIG. 9, magnified 1624 times. The limb aspect ratio was between 2:1 and 4:1. The staple fiber had a TFA of 25.3 g/g, a water imbibition of 110%, a filament tenacity of 18.4 cN/tex and an extension of 23%.

What is claimed is:

1. An absorbent article which comprises solid regenerated cellulosic staple fibers having a decitex in the range 0.5 to 5, substantially all of said fibers having a multi-limbed cross-section, wherein the length-to-width aspect retro of each limb in said multi-limbed cross-section is in the range 2:1 to 10:1, and substantially all of said fibers being of the same cross-sectional shape.

2. The absorbent article of claim 1 wherein said absorbent article additionally comprises other fibers different in cross-section from said solid regenerated cellulosic staple fibers.

3. The absorbent article of claim 1 wherein said fibers have a multi-limbed cross-section with three limbs.

4. The absorbent article of claim 1 wherein said fibers have a multi-limbed cross-section with four limbs.

5. The absorbent article of claim 1 wherein said length-to-width aspect ratio is in the range 2:1 to 7:1.

6. The absorbent article of claim 1 wherein said length-to-width aspect ratio is in the range 3:1 to 5:1.

7. The absorbent article of claim 1 wherein said fibers have a decitex in the range 1.5 to 4.0.

8. The absorbent article of claim 1 wherein said article consists solely of said solid regenerated cellulosic staple fibers.

9. The absorbent article of claim 1 wherein said article is a textile article.

10. The absorbent article of claim 9 wherein said article is a non-woven article.

11. The absorbent article of claim 9 wherein said article is a knitted or woven article.

12. The absorbent article of claim 1 wherein said article additionally comprises other fiber different in cross-section or material from said solid regenerated cellulosic staple fibers.

13. The absorbent article of claim 12 wherein said other fiber comprises cellulosic fiber.

14. The absorbent article of claim 12 wherein said other fiber comprises cellulosic fiber selected from the group consisting of standard viscose rayon and cotton.

15. The absorbent article of claim 12 wherein said other fiber comprises polyester fiber.

16. The absorbent article of claim 1 wherein said article is a tampon.

17. The absorbent article of claim 16 wherein said tampon is a longitudinally expanding tampon.

18. The absorbent article of claim 16 wherein said tampon is a radially expanding tampon.

* * * * *

UNITED STATES PATENT AND TRADEMARK OFFICE
CERTIFICATE OF CORRECTION

PATENT NO. : 5,634,914                           Page 1 of 3
DATED      : June 3, 1997
INVENTOR(S): Andrew G. Wilkes and Alan J. Bartholomew It is certified that error appears in the above-indentified patent and that said Letters Patent is hereby corrected as shown below:

In the Title, delete "Fibre" and insert in place thereof -- Fiber --.

Col. 1, line 20, delete "61-13812" and insert in place thereof -- 61-113812 --.

Col. 2, line 56, after "20" insert -- $\mu$m --.

Col. 2, line 61, delete "sulphate" and insert in place thereof -- sulfate --.

Col. 2, line 63, delete "sulphate" and insert in place thereof -- sulfate --.

Col. 3, line 4, delete "sulphate" and insert in place thereof -- sulfate --.

Col. 4, line 16, delete "sulphate" and insert in place thereof -- sulfate --.

Col. 4, line 17, delete "sulphate" and insert in place thereof -- sulfate --.

Col. 4, line 20, delete "millilitres" and insert in place thereof -- milliliters --.

Col. 4, line 39, delete "gram" and insert in place thereof -- grams --.

UNITED STATES PATENT AND TRADEMARK OFFICE
CERTIFICATE OF CORRECTION

PATENT NO. : 5,634,914
DATED : June 3, 1997
INVENTOR(S) : Andrew G. Wilkes and Alan J. Bartholomew It is certified that error appears in the above-indentified patent and that said Letters Patent is hereby corrected as shown below:

Col. 4, line 60, delete "sulphate" and insert in place thereof -- sulfate --.

Col. 5, line 12, delete "sulphate" and insert in place thereof -- sulfate --.

Col. 5, line 13, delete "sulphate" and insert in place thereof -- sulfate --.

Col. 5, line 53, delete "millimetres" and insert in place thereof -- millimeters --.

Col. 5, line 56, after "measures,", insert -- in --.

Col. 5, line 67, delete "RE" and insert in place thereof -- RH --.

Col. 7, line 11, delete "rigidify" and insert in place thereof -- modify --.

Col. 7, line 39, delete both occurrences of "sulphate" and insert in place thereof in both occurrences -- sulfate --.

Col. 10, line 57, delete the "." after the word "through".

Col. 10, line 65, delete "mi/min." and insert in place thereof -- ml/min. --.

UNITED STATES PATENT AND TRADEMARK OFFICE
CERTIFICATE OF CORRECTION

PATENT NO. : 5,634,914

DATED : June 3, 1997

INVENTOR(S) : Andrew G. Wilkes and Alan J. Bartholomew

It is certified that error appears in the above-indentified patent and that said Letters Patent is hereby corrected as shown below:

Col. 11, line 63, delete "sulphate" and insert in place thereof -- sulfate --.

Col. 12, line 8, delete "2:i" and insert in place thereof -- 2:1 --.

Col. 12, line 16, in Claim 1, delete "retro" and insert in placed thereof -- ratio --.

Signed and Sealed this

Eleventh Day of November, 1997

Attest:

BRUCE LEHMAN

Attesting Officer

Commissioner of Patents and Trademarks